US010457567B2

(12) United States Patent
Kamen et al.

(10) Patent No.: US 10,457,567 B2
(45) Date of Patent: *Oct. 29, 2019

(54) SYSTEMS AND METHODS FOR DISTRIBUTED UTILITIES

(71) Applicant: DEKA Products Limited Partnership, Manchester, NH (US)

(72) Inventors: Dean Kamen, Bedford, NH (US); Jason A. Demers, Manchester, NH (US); Kingston Owens, Bedford, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 61 days.

This patent is subject to a terminal disclaimer.

(21) Appl. No.: 14/269,742

(22) Filed: May 5, 2014

(65) Prior Publication Data

US 2014/0244042 A1    Aug. 28, 2014

Related U.S. Application Data

(63) Continuation of application No. 10/566,307, filed as application No. PCT/US2004/024335 on Jul. 28, 2004, now Pat. No. 8,718,827, and a continuation-in-part of application No. 10/714,683, filed on Nov. 13, 2003, now Pat. No. 7,340,879.

(60) Provisional application No. 60/518,782, filed on Nov. 10, 2003, provisional application No. 60/490,615, filed on Jul. 28, 2003, provisional application No. 60/425,820, filed on Nov. 13, 2002.

(51) Int. Cl.
| | | |
|---|---|---|
| C02F 1/00 | (2006.01) | |
| G05B 15/02 | (2006.01) | |
| G01D 4/00 | (2006.01) | |
| G01N 11/02 | (2006.01) | |
| G06Q 50/06 | (2012.01) | |
| G05D 7/06 | (2006.01) | |

(52) U.S. Cl.
CPC ............. *C02F 1/008* (2013.01); *G01D 4/004* (2013.01); *G01N 11/02* (2013.01); *G05B 15/02* (2013.01); *G05D 7/0629* (2013.01); *G06Q 50/06* (2013.01); *Y02B 90/242* (2013.01); *Y04S 20/322* (2013.01)

(58) Field of Classification Search
CPC ....... C02F 1/008; G05D 7/0629; G01N 11/02; G06Q 50/06; G01D 4/004; G05B 15/02; Y04S 20/322; Y02B 90/242
See application file for complete search history.

(56) References Cited

U.S. PATENT DOCUMENTS

2004/0025496 A1* 2/2004 Patterson, Jr. .......... F41H 11/00
60/254

* cited by examiner

*Primary Examiner* — Nathan L Laughlin
(74) *Attorney, Agent, or Firm* — Michelle Saquet Temple

(57) ABSTRACT

A monitoring system for distributed utilities. A generation device is provided for converting an available resource to a desired utility; the resource may be water, in which case the generator is a purifier for providing potable water, or, alternatively, the generator may convert a fuel to electrical power. In either case, an input sensor is provided for measuring input to the generation device, while an output sensor is provided for measuring consumption of output from the generation device. The monitoring system has a controller for concatenating measured input and consumption of output on the basis of the input and output sensors. Measured parameters are telemetered to a remote site where utility generation and use are monitored and may also be controlled.

5 Claims, 2 Drawing Sheets

SYSTEMS AND METHODS FOR DISTRIBUTED UTILITIES

CROSS REFERENCE TO RELATED APPLICATIONS

The present application is a continuation of U.S. patent application Ser. No. 10/566,307, filed Jan. 27, 2006 and entitled System and Methods for Distributed Utilities, now U.S. Pat. No. 8,718,827, issued May 6, 2014, which is a '371 Application of International Application Serial No. PCT/US2004/24335 filed on Jul. 28, 2004 and entitled Systems and Methods for Distributed Utilities, which claims priority from U.S. Provisional Patent Application Ser. No. 60/490,615 filed on Jul. 28, 2003 and entitled Systems and Methods for Distributed Utilities, and U.S. Provisional Patent Application Ser. No. 60/518,782 filed on Nov. 10, 2003 and entitled Locally Powered Water Distillation System, all of which are incorporated herein by reference in their entireties.

U.S. patent application Ser. No. 10/566,307, filed Jan. 27, 2006 and entitled Systems and Methods for Distributed Utilities, is also a continuation-in-part of U.S. patent application Ser. No. 10/714,683 filed on Nov. 13, 2003, and entitled Locally Powered Water Distillation System, now U.S. Pat. No. 7,340,879, issued Mar. 11, 2008, which claims priority to U.S. Provisional Patent Application Ser. No. 60/425,820, filed Nov. 13, 2002 and entitled Pressurized Vapor Cycle Liquid Distillation, U.S. Provisional Patent Application Ser. No. 60/490,615, filed Jul. 28, 2003 and entitled Systems and Methods for Distributed Utilities, and U.S. Provisional Patent Application Ser. No. 60/518,782, filed Nov. 10, 2003 and entitled Locally Powered Water Distillation System, each of which is hereby incorporated herein by reference in its entirety.

TECHNICAL FIELD

The present invention relates to the field of distributed utilities, and, more particularly, to distributed water purification systems and distributed power.

BACKGROUND ART

In many developing countries and remote areas without power plants and water purification plants, access to electricity and safe drinking water is a significant need. Often in such areas, poor financial resources, limited technical assets, and low population density does not make it feasible to build power plants and water purification plants to provide these resources to the population. In such circumstances, the use of distributed utilities may provide a solution. Distributed water purification systems, such as described in U.S. Provisional Application 60/425,820, and distributed electrical generators, such as diesel-powered internal combustion generators and generators based on the Stirling cycle, such as described in U.S. Pat. No. 6,253,550, may be used to provide electricity and safe drinking water without the expense and delays associated with building and maintaining utility plants and the infrastructure required to bring the electricity and safe drinking water and to its point of use. With such the use of such distributed utilities, however, comes the need to appropriately distribute these utilities to the people who need them and to monitor the operation and correct usage of these systems.

SUMMARY OF THE INVENTION

In accordance with preferred embodiments of the present invention, a monitoring system for distributed utilities is provided. The monitoring system has a generation device for converting an available resource to a desired utility. The available resource may be water, in which case the generator is a purifier for providing potable water. Alternatively, the generator may convert a fuel to electrical power. In either case, an input sensor is provided for measuring one or more characteristics of the input to the generation device, while an output sensor is provided for measuring consumption or other characteristic of output from the generation device. The monitoring system has a controller for concatenating measured input and consumption of output on the basis of the input and output sensors.

Where the generation device, in the case, for example, of a particular utility of a network, is a water purifier, the input sensor may be a flow rate monitor. The output sensor may be a water quality sensor including one or more of turpidity, conductivity, and temperature sensors. On the other hand, where the generation device is an electrical power generator, the input sensor may include a fuel consumption rate monitor and the output sensor may include an electrical usage meter.

The monitoring system may also have a telemetry module for communicating measured input and output parameters to a remote site, either directly or via an intermediary device such as a satellite, and, moreover, the system may include a remote actuator for varying operating parameters of the generator based on remotely received instructions. The monitoring system may also have a self-locating device, such as a GPS receiver, having an output indicative of the location of the monitoring system. In that case, characteristics of the measured input and output may depend upon the location of the monitoring system.

In accordance with further embodiments of the invention, a distributed network of utilities is provided, including sources of purified water and sources of electrical power. The distributed network has generators for converting a resource into a useful utility, input sensors for measuring inputs to respective generators, output sensor for measuring consumption of output from respective generators, and a telemetry transmitter for transmitting input and output parameters of a specified generator. Finally, the distributed network has a remote processor for receiving input and output parameters from a plurality of utility generators.

In accordance with yet another embodiment of the invention, a method is provided for supplying distributed utilities. The method has steps of providing a generator to a user, monitoring at least one index of generator usage to supply a utility, and charging the user on the basis of the index of generator usage.

In accordance with other aspects of the present invention, methods are provided for assembling monitoring systems that monitor input to, and consumption of output from, a generating device. These methods include coupling sensors to a controller of the generating device, and communication channels between the controller and a monitoring station via a telemetry module.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Monitoring

Figure 1:
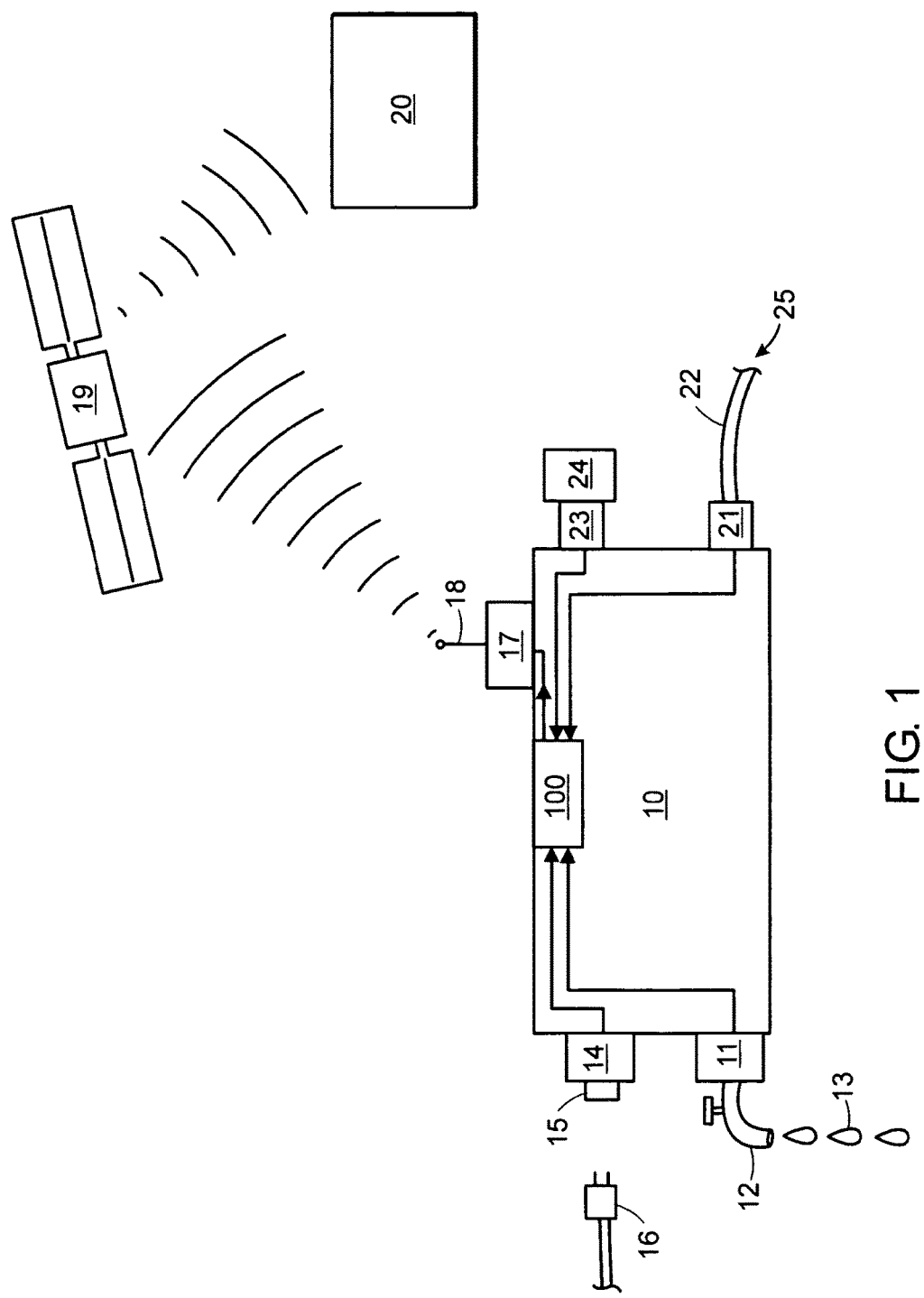
FIG. 1 is a depiction of a monitoring system for distributed utilities in accordance with embodiments of the present invention.

Referring first to FIG. 1, preferred embodiments of the present invention provide for monitoring generation device 10. Generation device 10 can be any distributed utility generation device, such as a water purification system, an electrical generator, or other utility generation device, or a combination of these. Generation device 10 may typically be characterized by a set of parameters that describe its current operating status and conditions. Such parameters may include, without limitation, its temperature, its input or output flux, etc., and may be subject to monitoring by means of sensors, as described in detail below.

In the case in which generation device 10 is a water purification device, source water enters the generation device 10 at inlet 22 and leaves the generation device at outlet 12. The amount of source water 25 entering generation device 10 and the amount of purified water 13 leaving generation device 10 can be monitored through the use of one or more of a variety of sensors commonly used to determine flow rate, such as sensors for determining them temperature and pressure or a rotometer, located at inlet sensor module 21 and/or at outlet sensor module 11, either on a per event or cumulative basis. Additionally, the proper functioning of the generation device 10 can be determined by measuring the turpidity, conductivity, and/or temperature at the outlet sensor module 11 and/or the inlet sensor module 21. Other parameters, such as system usage time or power consumption, either per event or cumulatively, can also be determined. A sensor can be coupled to an alarm or shut off switch that may be triggered when the sensor detects a value outside a pre-programmed range.

When the location of the system is known, either through direct input of the system location or by the use of a GPS location detector, additional water quality tests may be run based on location, including checks for known local water contaminates, utilizing a variety of detectors, such as antibody chip detectors or cell-based detectors. The water quality sensors may detect an amount of contaminates in water. The sensors can be programmed to sound an alarm if the water quality value rises above a pre-programmed water quality value. The water quality value is the measured amount of contaminates in the water. Alternatively, a shut off switch may turn off the generation device if the water quality value rises about a pre-programmed water quality value.

Further, scale build-up in the generation device 10, if any, can be determined by a variety of methods, including monitoring the heat transfer properties of the system or measuring the flow impedance. A variety of other sensors may be used to monitor a variety of other system parameters.

In the case in which generation device 10 is an electrical generator, either alone or in combination with a water purification device or other device, fuel enters the generation device from a tank, pipe, or other means through fuel inlet 24. The amount of fuel consumed by generation device 10 can be determined through the use of a fuel sensor 23, such as a flow sensor. Electricity generated, or in the case of a combined electrical generator and water purification device, excess electricity generated can be accessed through electricity outlet 15. The amount of electricity used, either per event of cumulatively, may be determined by outlet sensor module 14. A variety of other sensors may be used to monitor a variety of other system parameters.

In either of the cases described above, input sensor modules 21 and 23 as well as output sensor modules 11 and 14 may be coupled to a controller 100, electrically or otherwise, in order to process, concatenate, store, or communicate the output values of the respective sensor modules as now described in the following section.

Communications

The sensors described above may be used to monitor and/or record the various parameters described above onboard the generation device 10, or in an alternative embodiment of the present invention, the generation device 10 may be equipped with a communication system 17, such as a cellular communication system. The communication system 17 could be an internal system used solely for communication between the generation device 10 and the monitoring station 20. Alternatively, the communication system 17 could be a cellular communication system that includes a cellular telephone for general communication through a cellular satellite system 19. The communication system 17 may also employ wireless technology such as the Bluetooth® open specification. The communication system 17 may additionally include a GPS (Global Positioning System) locator.

Communication system 17 enables a variety of improvements to the generation device 10, by enabling communication with a monitoring station 20. For example, the monitoring station 20 may monitor the location of the generation device 10 to ensure that use in an intended location by an intended user. Additionally, the monitoring station 20 may monitor the amount of water and/or electricity produced, which may allow the calculation of usage charges. Additionally, the determination of the amount of water and/or electricity produced during a certain period or the cumulative hours of usage during a certain period, allows for the calculation of a preventative maintenance schedule. If it is determined that a maintenance call is required, either by the calculation of usage or by the output of any of the sensors used to determine water quality, the monitoring station 20 can arrange for a maintenance visit. In the case that a GPS (Global Positioning System) locator is in use, monitoring station 20 can determine the precise location of the generation device 10 to better facilitate a maintenance visit. The monitoring station 20 can also determine which water quality or other tests are most appropriate for the present location of the generation device 10. The communication system 17 can also be used to turn the generation device 10 on or off, to pre-heat the device prior to use, or to deactivate the system in the event the system is relocated without advance warning, such as in the event of theft.

This information can be advantageously monitored through the use of a web-based utility monitoring system, such as those produced by Teletrol Systems, Inc. of Bedford, N.H.

Distribution

Figure 2:
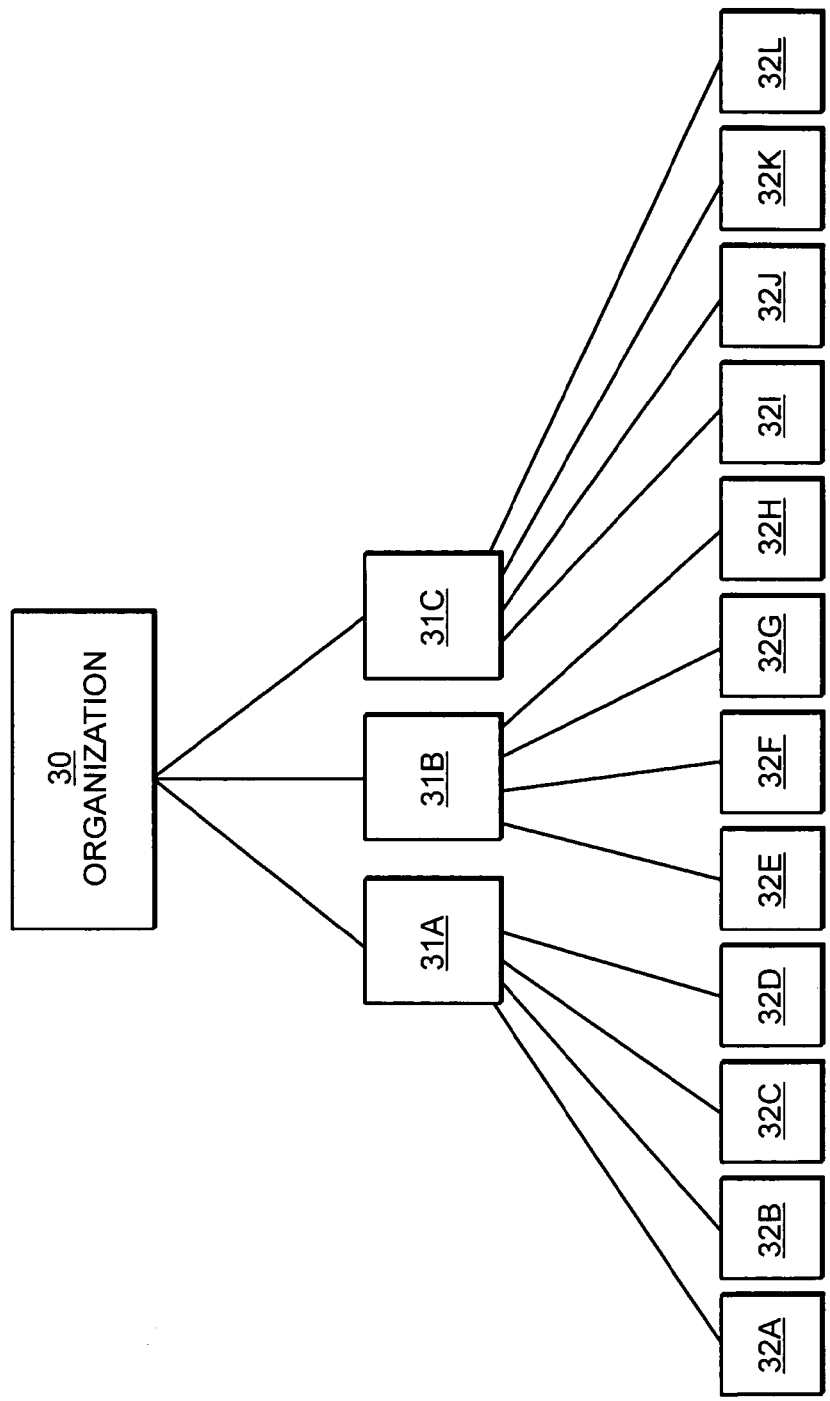
FIG. 2 is a depiction of a distribution system for utilities in accordance with embodiments of the present invention.

The use of the monitoring and communication system described above facilitates the use of a variety of utility distribution systems. For example, with reference to FIG. 2, an organization 30, such as a Government agency, non-governmental agency (NGO), or privately funded relief organization, a corporation, or a combination of these, could provide distributed utilities, such as safe drinking water or electricity, to a geographical or political area, such as an entire country. The organization 30 can then establish local distributors 31A, 31B, and 31C. These local distributors could preferably be a monitoring station 20 described above. In one possible arrangement, organization 30 could provide some number of generation devices 10 to the local distributor 31A, etc. In another possible arrangement, the organization 30 could sell, loan, or make other financial arrangements for the distribution of the generation devices 10. The local distributor 31A, etc. could then either give these generation devices to operators 32A, 32 B, etc., or provide the generation devices 10 to the operators though some type of financial arrangement, such as a sale or micro-loan.

The operator 32 could then provide distributed utilities to a village center, school, hospital, or other group at or near the point of water access. In one preferred embodiment, when the generation device 10 is provided to the operator 32 by means of a micro-loan, the operator 32 could charge the end users on a per-unit bases, such as per watt hour in the case of electricity or per liter in the case of purified water. Either the local distributor 31 or the organization 30 may monitor usage and other parameters using one of the communication systems described above. The distributor 31 or the organization 30 could then recoup some of the cost of the generation device 10 or effect repayment of the micro-loan by charging the operator 32 for some portion of the per-unit charges, such as 50%. The communication systems described additionally can be used to deactivate the generation device 10 if the generation device is relocated outside of a pre-set area or if payments are not made in a timely manner. This type of a distribution system may allow the distribution of needed utilities across a significant area quickly, while then allowing for at least the partial recoupment of funds, which, for example, could then be used to develop a similar system in another area.

In view of the foregoing, it will therefore be understood that the scope of the invention as defined in the following claims is not limited to the embodiments described herein, and that the above and numerous additional variations and modifications could be made thereto without departing from the scope of the invention.

What is claimed is:

1. A method for monitoring a water purification device comprising:
   providing a water purification device for converting an available resource to a desired utility, the water purification device characterized by a plurality of operating parameters;
   coupling an input sensor for measuring the available resource entering the water purification device;
   coupling an output sensor for measuring the amount of desired utility leaving the water purification device;
   coupling a local controller to the input and output sensor for concatenating the measured available resource entering and the amount of desired utility leaving the water purification device on the basis of the input and output sensors;
   providing a remote controller for modifying the operation of the water purification device based on the concatenated measured available resource entering and desired utility leaving the water purification device;
   providing a self-locating device having an output to the remote controller indicative of a geographical location of the water purification device;
   providing communication between a telemetry module and the remote controller; and
   providing communication between the telemetry module and a monitoring station,
   wherein the self-locating device is a global positioning system, and
   wherein the remote controller modifies operation of the water purification device based on the geographical location of the water purification device.

2. A monitoring system for distributed utilities, the monitoring system comprising:
   a water purification device for converting an available resource to a desired utility, the water purification device characterized by a plurality of operating parameters;
   an input sensor for measuring the available resource entering the water purification device;
   an output sensor for measuring the amount of the desired utility leaving the water purification device;
   a local controller for concatenating the measured available resource entering and the desired utility leaving the water purification device on the basis of the input and output sensors;
   a remote controller for modifying operation of the water purification device; and
   a self-locating device having an output to the remote controller indicative of a geographical location of the water purification device, wherein the remote controller modifies operation of the water purification device based on the geographical location of the water purification device.

3. The monitoring system of claim 2, further comprising at least one sensor for measuring at least one parameter of the plurality of operating parameters of the water purification device.

4. The monitoring system of claim 2, further comprising a telemetry module for communicating measured input and output parameters to a remote site.

5. The monitoring system of claim 2, further comprising a remote actuator for varying operating parameters of the generation device based on remotely received instructions.

* * * * *